US008895075B2

(12) United States Patent
Desai

(10) Patent No.: US 8,895,075 B2
(45) Date of Patent: Nov. 25, 2014

(54) HERBOMINERAL FORMULATION FOR TREATING SICKLE CELL DISEASE

(76) Inventor: Atul M. Desai, Vyara (IN)

( * ) Notice: Subject to any disclaimer, the term of this patent is extended or adjusted under 35 U.S.C. 154(b) by 740 days.

(21) Appl. No.: 12/677,308

(22) PCT Filed: Sep. 16, 2008

(86) PCT No.: PCT/IN2008/000590
§ 371 (c)(1),
(2), (4) Date: Mar. 10, 2010

(87) PCT Pub. No.: WO2009/063499
PCT Pub. Date: May 22, 2009

(65) Prior Publication Data
US 2010/0189814 A1    Jul. 29, 2010

(30) Foreign Application Priority Data

Sep. 20, 2007 (IN) .......................... 1620/MUM/2007
Mar. 19, 2008 (IN) ........................... 564/MUM/2008

(51) Int. Cl.

| | | |
|---|---|---|
| A61K 33/00 | (2006.01) | |
| A61K 33/04 | (2006.01) | |
| A61K 33/26 | (2006.01) | |
| A61K 33/28 | (2006.01) | |
| A61K 36/00 | (2006.01) | |
| A61K 36/27 | (2006.01) | |
| A61K 36/59 | (2006.01) | |
| A61K 36/67 | (2006.01) | |
| A61K 36/8965 | (2006.01) | |
| A61K 36/9068 | (2006.01) | |
| A61P 7/00 | (2006.01) | |
| A61K 33/12 | (2006.01) | |
| A61K 36/185 | (2006.01) | |
| A61K 36/28 | (2006.01) | |
| A61K 36/48 | (2006.01) | |
| A61K 36/906 | (2006.01) | |
| A61K 45/06 | (2006.01) | |

(52) U.S. Cl.
CPC ................. *A61K 33/26* (2013.01); *A61K 33/04* (2013.01); *A61K 33/12* (2013.01); *A61K 33/28* (2013.01); *A61K 36/185* (2013.01); *A61K 36/28* (2013.01); *A61K 36/48* (2013.01); *A61K 36/59* (2013.01); *A61K 36/67* (2013.01); *A61K 36/8965* (2013.01); *A61K 36/906* (2013.01); *A61K 45/06* (2013.01)

USPC .......... 424/646; 424/644; 424/703; 424/714; 424/724; 424/725; 424/734; 424/756

(58) Field of Classification Search
None
See application file for complete search history.

(56) References Cited

U.S. PATENT DOCUMENTS

| | | |
|---|---|---|
| 5,449,516 A | 9/1995 | de Araujo |
| 5,800,819 A | 9/1998 | Wambebe et al. |
| 2006/0045923 A1 | 3/2006 | Hingorani et al. |
| 2006/0246161 A1 | 11/2006 | Xing et al. |

FOREIGN PATENT DOCUMENTS

| | | |
|---|---|---|
| FR | 2 855 056 A | 11/2004 |
| GB | 2 314 270 A | 12/1997 |

OTHER PUBLICATIONS

Kapoor, Some observations on the metal-based preparations in the Indian Systems of Medicine, Indian Journal of Traditional Knowledge (2010), vol. 9, No. 3, pp. 562-575.*
Sharma et al., Problems associated with clinical trials of Ayurvedic medicines, Brazilian Journal of Pharmacognosy (2010), vol. 20, No. 2, pp. 276-281.*
Lab Tests Online AU, "Sickle cell anaemia" (2011) [retrieved Mar. 25, 2012], retrieved from the internet <URL:http://www.labtestsonline.org.au/understanding/conditions/sickle>.*
IUPAC Compendium of Chemical Terminology (2012), "amount concentration, c", doi:10.1351/goldbook.A00295.*
IUPAC Compendium of Chemical Terminology (2012), "concentration", doi:10.1351/goldbook.C01222.*
International Search Report, Jun. 9, 2009, from International Phase of the instant application.

* cited by examiner

*Primary Examiner* — Abigail Fisher
*Assistant Examiner* — Frank Choi
(74) *Attorney, Agent, or Firm* — Jackson Patent Law Office

(57) ABSTRACT

A herbomineral composition for the treatment of sickle cell disease is described in the present invention. The herbo mineral composition include some herbal ingredients such as Jaiphal, Sunthi, Jivanti, Haritaki, Guduchi, Shatavari, Dadima, Pippali, along with the therapeutic minerals such as Abrakha Bhasma and Loha Bhasma at suitable concentrations to obtain synergistic anti sickling activity. The composition exhibited up to 60-87% antisickling activity on RBCs in 'vitro' at various concentrations. Patients treated with this composition found relief from most of the severe symptoms of sickle cell disease and sickle cell anemia, and had excellent improvement in quality of life.

14 Claims, 2 Drawing Sheets

HERBOMINERAL FORMULATION FOR TREATING SICKLE CELL DISEASE

CROSS-REFERENCE TO RELATED APPLICATIONS

This application is U.S. National Stage Entry of International Application PCT/IN2008/000590, which claims priority benefits of Indian Application 1620/MUM/2007 filed 20, Sept. 2007 and Indian Application 564/MUM/2008 filed 19, Mar. 2008.

FIELD OF INVENTION

The present invention deals with an oral formulation for the treatment of sickle cell disease. The invention particularly deals with the treatment of patients with mild to moderate severity of symptoms and patients with sickle cell trait with a herbomineral composition.

BACKGROUND OF THE INVENTION

Sickle cell disease is a genetic disorder which affects the red blood cells (RBCs). The RBCs of people with sickle cell disease contain a different form of hemoglobin called haemoglobin 'S'. This is an abnormal type of hemoglobin and RBCs containing this hemoglobin become sickle shaped. They also become stiff and due to their distorted shape they have difficulty in passing through small blood vessels. When these sickle cells, thus block the blood vessels, less blood reaches that part of the body. Tissue that does not receive the normal blood flow eventually gets damaged. This is the main cause of the various complications including increased incidence of infections encountered in sickle cell disease.

The normal RBCs containing normal hemoglobin (called 'Hemoglobin A') not only are soft and round but also live up to about 120 days before new ones replace them. However, the RBCs from people suffering from sickle cell disease hardly have a life of about 10 -20 days. The bone marrow can not make the new red blood cells fast enough to replace the dying ones. This results in severe anemia, which is one of the main symptoms of this disease. Sickle cell anemia affects millions of people worldwide.

Sickle cell disease is an inherited, life-long condition. People who have sickle cell anemia are born with it. They inherit two copies of the sickle gene from each parent. Sickle cell disease is prevalent world over including India. The major features of the sickle cell disease encountered in these patients include chronic fatigue, severe anemia, pain crises, bacterial infections, lung, liver and heart injury, leg ulcers, damage to the eye, inflammation of the hands and feet, arthritis, splenomegaly and chronic lung infections etc.

Sickle cell trait is an inherited condition in which both Hemoglobin A and Hemoglobin S are produced in Red Blood Cells, always more 'A' than 'S'. people with Sickle cell trait may also develop some complications at a later stage in life. Under unusual circumstances serious morbidity and mortality can result from polymerization of de-oxy hemoglobin S; these complications include increased urinary tract infections in women, gross hematuria, complications of hyphema, splenic infarction with altitude hypoxia or exercise and life threatening complications of exercise, excertional heat illness or idiopathic sudden death. In addition, certain disease associations have been noted with sickle cell trait—such as early end stage renal failure, renal medullary carcinoma and polycystic kidney disease.

Though efforts have been made to control many of the symptoms and complications of the disease, the results are far from satisfactory in providing lasting cure and comfort to the sickle cell patient. Usually the health maintenance for these patients starts with early diagnosis, preferably in the newborn period and includes penicillin prophylaxis, vaccination against potential bacterial disease and folic acid supplementation. Treatment of complications often includes antibiotics, pain management, intravenous fluids and surgery all backed by psycho-social support. Blood transfusions help sickle cell disease patients by reducing recurrent pain crisis, risk of stroke and other complications. Because blood cells contain iron, and there is no natural way of eliminating excess iron, patients who receive repeated blood transfusions accumulate iron in the body till it reaches toxic levels.

A constant search is going on to find a substance which can stop sickling of RBCs or which can at least offer lasting symptomatic relief to a patient with sickle cell disease. One of the most promising drugs for this condition was Hydroxyurea, which is essentially an anti-cancer drug. Hydroxyurea has been shown to reduce the painful crises and acute chest syndrome in adults and to lessen the need for blood transfusions. Hydroxyurea seems to work by increasing the fetal hemoglobin in the RBCs. But being a potent anti-cancer drug, it has its own side effects. The major side effects of Hydroxyurea include decreased production of platelets, red blood cells and white blood cells. The effects of long term Hydroxyurea is yet to be established.

Bone marrow transplantation is another procedure which is being tried in sickle cell disease, mainly in severely affected children. Though it may give dramatic results, its routine use is not possible because of the complications associated with the procedure besides the high cost and the need for highly sophisticated infrastructure and appropriate donors.

Efforts are being made to search for natural and herbal products which can offer therapeutic effect in sickle cell disease without producing undue adverse effects.

Vanillin, a food additive, has been evaluated as a potential agent to treat sickle cell disease. Studies have indicated moderate antisickling activity when compared to other aldehydes. Abraham et al; PMID2001455.

A phytochemical formulation has been patented in US by National Institute for Pharmaceutical Research and Development Federal Ministry of Science and Technology (Ahuja, NG). The composition is a cold water extraction product of a mixture containing Piper guineenses seeds, Pterocarpusosum stem, Eugenia caryophyllum fruit, Sorghumbicolor leaves and potash. Though promising, more clinical studies are required before the safety, efficacy of the formulation could be established. (U.S. Pat. No. 5,800,819 )

There is also a mention of hydration of sickle erythrocytes using a herbal extract (pfaffia paniculata) in vitro (British J.Haematology (2000 ); 111359-362)

Sickle cell disease is an international health problem and truly a global challenge. Hence efforts are being made to find out an ideal therapy which is effective and at the same time also safe. But so far none of the medications or procedures as described earlier have come anywhere close to what is desirable.

BRIEF SUMMARY OF THE INVENTION

According to an aspect of the present invention, there is a herbomineral composition for the treatment of sickle cell disease. The composition comprises Abrakha Bhasma (Calyx of Mica), Jaiphal (Myristica fragrans Houtt), Sunthi (Zingiber officinal Roscoe), Jivanti Ghana (Leptadenia reticulate), Haritaki Ghana (Terminalia chebula), Guduchi Ghana (Tinospora cordifolia), Shatavari Ghana (Asparagus racemosus), Dadima (Punica granatum Linn), Pippali (Piper longum Linn), and Loha Bhasma (Calyx of Iron).

According to another aspect of the present invention, there is a method of treating sickle cell disease. The method comprises orally administering to a human in need of treatment for sickle cell disease a herbomineral composition comprising Abrakha Bhasma (Calyx of Mica), Jaiphal (Myristica fragrans Houtt), Sunthi (Zingiber officinal Roscoe), Jivanti Ghana (Leptadenia reticulate), Haritaki Ghana (Terminalia chebula), Guduchi Ghana (Tinospora cordifolia), Shatavari Ghana (Asparagus racemosus), Dadima (Punica granatum Linn), Pippali (Piper longum Linn), and Loha Bhasma (Calyx of Iron).

According to yet another aspect of the present invention, there is a method of treating sickle cell disease, the method comprising orally administering to a human in need of treatment for sickle cell disease a herbomineral composition comprising Kajjali (made from equal proportion of Mercury and Ghandhak), Abrakha Bhasma (Calyx of Mica), Jaiphal (Myristica fragrans Houtt), Sunthi (Zingiber officinal Roscoe), Jivanti Ghana (Leptadenia reticulate), Haritaki Ghana (Terminalia chebula), Guduchi Ghana (Tinospora cordifolia), Shatavari Ghana (Asparagus racemosus), Dadima (Punica granatum Linn g), Pippali (Piper longum Linn), Loha bhasma (Calyx of Iron).

DETAILED DESCRIPTION OF THE PREFERRED EMBODIMENTS OF THE INVENTION

Figure 1:
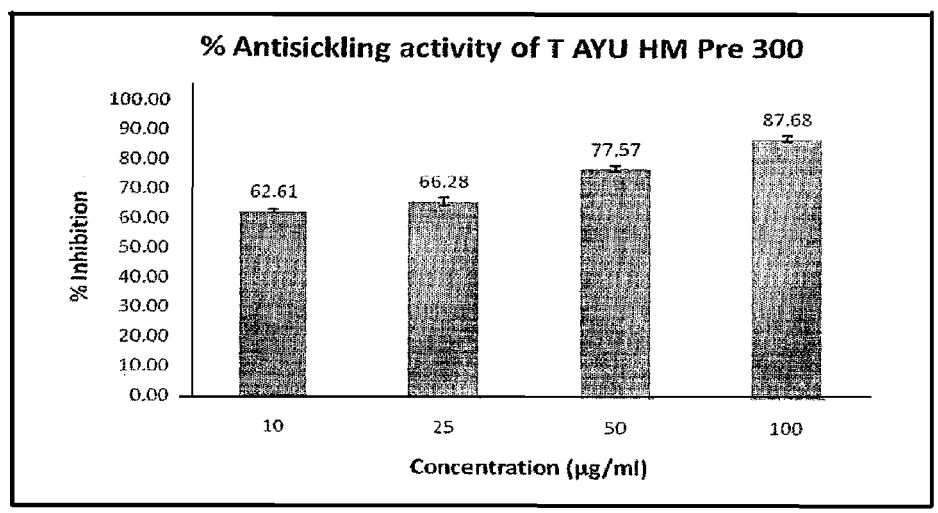
FIG. 1 (i.e Graph 1) depicts antisickling activity in terms of sickle cell count (percentage) on being treated with a formulation in accordance with a preferred embodiment of the present invention.
Figure 2:
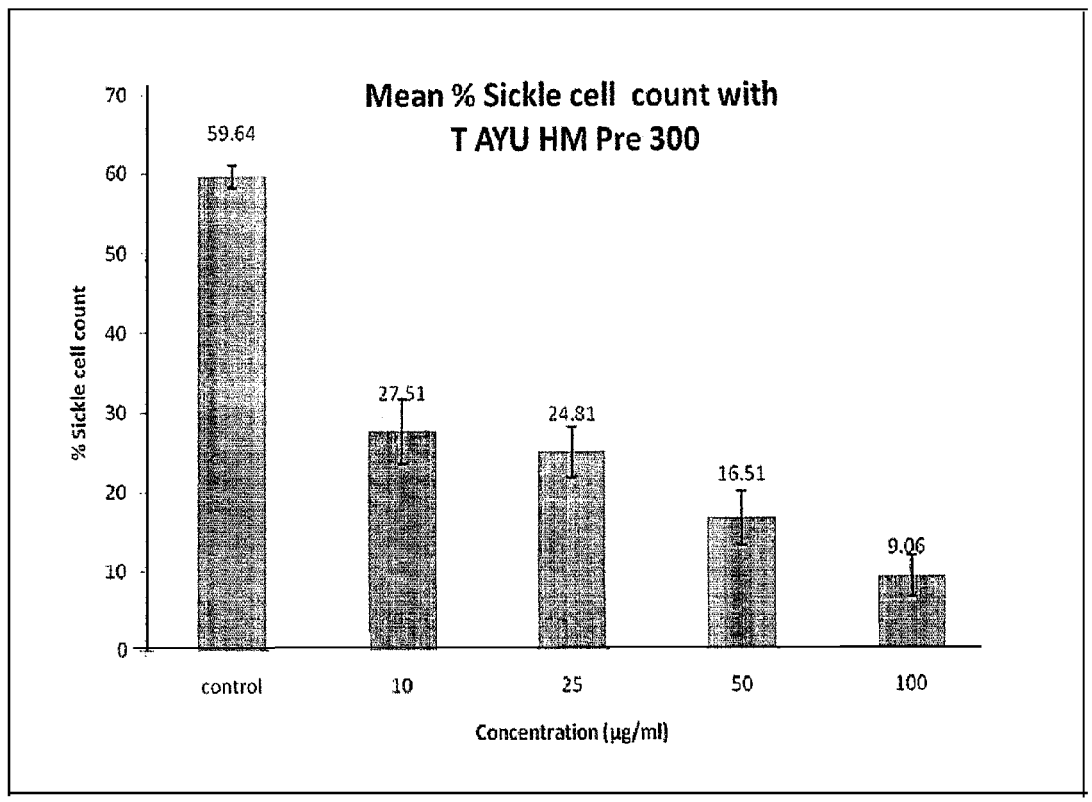
FIG. 2 (i.e Graph 2) depicts the antisickling efficacy of formulation percentage in terms of inhibition of sickling.

A preferred embodiment of the present invention includes a novel herbo-mineral formulation for treating sickle cell disease. The formulation includes the following ingredients and preferred concentrations of the ingredients:

TABLE 1

| | INGREDIENTS | Preferred Amounts |
|---|---|---|
| Sunthi | [Zingiber officinal Roscoe] | 25 mg |
| Jivanti Ghana | [Leptadenia reticulate] | 37.5 mg |
| Haritaki Ghana | [Terminalia chebula] | 25 mg |
| Guduchi Ghana | [Tinospora cordifolia] | 37.5 mg |
| Shatavari Ghana | [Asparugus racemosus] | 25 mg |
| Dadima | [Punica granatum Linn] | 12.5 mg |
| Pippali | [Piper longum Linn] | 37.5 mg |
| Lohabhasma | Calyx of Iron [Krantloha-Fe3O4] | 12.5 mg |

We refer to this formulation as T AYU HM PRE-300.

A brief description of the ingredients used in the present formulation (T AYU HM Pre-300) is as follows:

Brakha Bhasma (Mica Ash);

It is found to be useful for anemia, splenomegaly, Aging and general debility. It is supposed to be also an energizer (Rasrana Sammucchay in Hindi (Part 1) Prof Dattatray Kulkarni).

Loha Bhasma: (Iron Ash):

The indications include Iron deficiency Anaemia, Leukemia, Bone marrow depression It is also known to strengthen muscle and nerve tissues .(Bhartiya Rasashastra in Gujarati by Vaidya Bapalal.)

Haritaki (Terminalia Chebuta):

The part commonly used is the fruit. Haritaki is an excellent drug for constipation. The clinical use include-infectious disease such as chronic ulcers, leucorrhoea, pyorrhea, and fungal infections of the skin. (CHEMEXIL-Selected Medicinal plants of India, 1992)

Shunthi: (Ginger Officianale):

Parts used; Rhizomes. Ginger is known to have significant antiemetic and anti vertigo effects. The other main indications include Bronchial asthma, Rheumatic disorders, common cold and motion sickness. (Central Research Institute (AYUSH) Bhubaneshwar, "efficacy of Ginger')

Shatavari: (Asparagus Racemosus):

Parts used: Root and Leaves. It is used as a general tonic and aphrodisiac. Also found to be useful for acidity. (Satyavati, Pharmacology Review 1983, p-123).

Jivanti (Leptadenia Reticulate W):

Parts used: Roots. It is used for multiple clinical indications such as Diminished lactation, habitual abortion, skin infections and as a stimulant, galactogogue, and tonic.(Medicinal-Plant of India ,ICMR, New Delhi, 1976, Part 1.)

Dadima: (Punica Granatum Linn)

Parts used: Fruit rand, roots, root bark, Flowers mainly used for Helminthiasis: Other indications include—reduced appetite, diarrhoea, Nausea, vomiting, Epistaxis (Hamdard XXVI; p-10 Antidiarrhoeal & antidysentric.)

Guduchi (Tinospora Cordifolia)

Parts used: Roots, Stems, Leaves. Used in the compound formulation for treatment of Jaundice, Rheumatoid Arthritis, Gout, Diabetes and General Weakness. (Planta Medica 983, Vol. 48, p. 278; Indian journal of Pharmaceutical Sciences April-May 1985, p. 65)

Pippali (Piper Longum Linn)

Parts used: Root, Stem and Fruit. Used for the treatment of Malaria, bronchial asthma, and Hepatitis. Also gives good relief in dyspepsia and flatulence.

Jaiphal (Myristica Fragrans Houtt)

Parts used: Seed. Known to possess potent antibacterial, anti-inflammatory, anlgesic and anti-oxidant property besides having anticonvulsant and hypnotic effects. Also used as carminative, antiflatulent and tonic for heart and brain.

The unique combination of the above ingredients at individual concentrations as mentioned above arrived at after a lot of trials has demonstrated a potent and synergistic anti-sickling activity in vitro well as in vivo.

In-Vitro Testing For Anti-Sickling Activity: Blood samples were collected from the patients identified positive for sickle cell anemia.

Anti drepanocytary activity of the test formulations were evaluated using Emmel's test.

Emmel's Test Protocol:

A. For control group 20 micro·L. of blood sample was treated with 20 micro·L of physiologic solution (0.9 % NaCl solution) to maintain the osmotic condition of the cellular medium and avoid precocious hemolysis of red blood cells.

B. For treatment group 20 micro. L. of blood sample was incubated with 20 micro.L of the polyherbal formulation containing 115 mg/ml, 30 mg/ml and 45 mg/ml concentrations of polyherbal formulation respectively.

A drop of A/B was put on slide and hermetically covered by cover glass using vacuum grease.

In order to ensure complete anaerobic conditions the slides were placed in vacuum desiccator and then transferred to incubator (37 C) for 24 hours. After 24 hours in anaerobic condition, RBCs undergo deoxygenation and adopt sickle shape due to polymerization and precipitation of Hemoglobin S.

The slides were observed for the presence of sickle cells count using Photo microscopy with magnification at 45× digitalization of images with DTV250 software and recording with DIVIX software for the count of the number of sickle cells present.

TABLE 2

Details of the patient under study with their disease characteristic.

| Sr. No. | Age | Treatment | Status |
|---------|-----|-----------|--------|
| 01 | 13 | Untreated | SCD |
| 02 | 16 | Untreated | SCD |
| 03 | 13 | Untreated | SCD |
| 04 | 12 | Untreated | SCD |
| 05 | 32 | Untreated | SCD |

Results

With the followed test protocol the blood samples undergoes sickling in deoxygenated conditions induced by anaerobic conditions of Emmel's test protocol.

The test formulations showed significant inhibition of sickling of RBCs. The formulation of the present invention revealed 62.61+−1.44%, 66.28+−1.11%, 77.57+−1.19%, and 87.68 +−0.95% anti sickling activity at concentrations of 10 ug/ml, 25 ug/ml, 50 ug/ml, and 100 ug/ml respectively. (Table 3, 4; Graph 1, 2)

Thirty patients suffering from sickle cell disease with symptoms were successfully treated with the herbomineral combination of the present invention. The usual dose was twice a day of oral preparation containing ingredients as per the concentrations mentioned (table 1) preferably in the tablet form.

Children could be given the same formulation once a day (ie. half of normal the adult dose).

There was dramatic improvements in the patients conditions especially with respect to reduction or freedom from symptoms. No toxicity due to the medicine was observed in any of the patients The minimum duration of therapy required in most of the cases was 3 months while severe cases may require long term or even life long therapy with the formulation. There was improvement, to the extent of almost 90% in the various symptoms such as "hand & chest syndrome' (ie chest pain, shoulder pain, breathlessness, chest infection), relief from pain and tenderness of calf muscle, leg ulcer, headache, loss of appetite colic backache etc.

There was distinct improvement in the hematological parameters such as RBC count hemoglobin levels, WBC counts, platelet counts, PCV etc. The need for blood transfusions is also considerably reduced.

This novel herbomineral formulation of the present invention not only reduces painful episodes in the sickle cell patients and also protects the vital organs. The formulation has been found to be safe and well tolerated in all the patients.

Hence the present invention fills the void in the treatment of sickle cell disease and enhances quality of life of these patients.

EXAMPLE 2

In another embodiment, to the herbomineral ingredients described above 'Kajjali'—which is made from equal portion of mercury and 'gandhak' is added. The preferred concentration of the Kajjali is approximately 50 mg. Addition of Kajjali contributes to antisickling activity. Composition containing Kajjali could be used along with other ingredients as described in Example 1, in cases where substances like Kajjali are tolerated by the patients even on long term use. The preferred composition of herbomineral ingredients containing Kajjali is as shown below:

| | INGREDIENTS | Preferred Amounts |
|---|---|---|
| KAJJALI | made from equal portion of Mercury and Ghandhak | 50 mg. |
| Abrakha Bhasma | Calyx of Mica | 12.5 mg |
| Jaiphal | [*Myristica fragrans houtt*] | 25 mg |
| Sunthi | [*Zingiber officinal Roscoe*] | 25 mg |
| Jivanti Ghana | [*Leptadenia reticulate*] | 25 mg |
| Haritaki Ghana | [*Terminalia chebula*] | 25 mg |
| Guduchi Ghana | [*Tinospora cordifolia*] | 12.5 mg |
| Shatavari Ghana | [*Asparugus racemosus*] | 12.5 mg |
| Dadima | [*Punica granatum Linn.*] | 12.5 mg |
| Pippali | [*Piper longum linn*] | 37.5 mg |
| Lohabhasma | Calyx of Iron [Krantloha-Fe3O4] | 12.5 mg |

A brief description of Kajjali is as follows:

Kajjali:

When Sulphur (Ghandhaka) is added to Mercury (Parada) and triturated without adding liquid till it becomes a very fine black powder it is called Kajjali; Made from equal portion of Mercury and Gandhak. It is considered to be an Ayurvedic antibiotic or antibacterial medicine. (Rasatarangini, taranga2; 27) It is believed that the combination of these metals carry the actions of the herbs to the subtle channels and tissue of the body.

This formulation also exhibited good antisikling activity n vitro as well as in vivo-ie. in patients suffering from sickle cell disease.

Thirty patients suffering from sickle cell disease with symptoms were successfully treated with this herbomineral combination containing Kajjali. The usual dose was twice a day of oral preparation containing ingredients as per the concentrations mentioned, preferably in the tablet form.

Children could be given once a day (ie. half of normal the adult dose) of the same composition. Dramatic improvements in the patients conditions were observed with respect to—reduction or freedom from symptoms. The minimum duration of therapy required in most of the cases was 3 months while severe cases may require long term or even life long therapy. There was excellent improvement in the "hand & Chest syndrome' (ie chest pain, shoulder pain, breathlessness, chest infection). There was more than 50% improvement in avascular necrosis of Femur (AVNF). There was excellent relief from pain and tenderness of calf muscle (more than 75%). There was significant improvement in almost all the signs and symptoms which include splenomegaly, jaundice, pallor, backache, abdominal colic, loss of appetite, and headache. etc. There was distinct improvement in the hematological parameters such as RBC count, hemoglobin levels, WBC counts, platelet counts, PCV, MCHC etc. and the need for blood transfusions is also considerably reduced.

TABLE 4

Comparison of effect of Herbomineral formulation
T AYU HM Pre 300 On test blood samples
% Sickle cells

| Blood Samples | Pretreatment control | Post treatment | | | |
| --- | --- | --- | --- | --- | --- |
| | | 10 µg/ml | 25 µg/ml | 50 µg/ml | 100 µg/ml |
| 1 | 57.59 | 27.23 | 27.21 | 14.96 | 8.27 |
| 2 | 59.73 | 28.53 | 24.16 | 14.08 | 6.64 |
| 3 | 59.06 | 30.71 | 25.15 | 22.29 | 10.31 |
| 4 | 60.43 | 30.39 | 27.71 | 16.62 | 13.10 |
| 5 | 61.41 | 20.69 | 19.81 | 14.58 | 6.99 |
| Mean % sickle cells | 59.64 | 27.51 | 24.81 | 16.51 | 9.06 |
| SD | 1.44 | 4.07 | 3.15 | 3.37 | 2.67 |
| SEM | 0.51 | 1.44 | 1.11 | 1.19 | 0.95 |
| P Value | — | 0.00 | 0.14 | 0.00 | 0.00 |
| % INHIBITION | — | 62.61 | 66.28 | 77.57 | 87.68 |

I claim:

1. An oral herbomineral composition for the treatment of sickle cell disease, the composition comprising an effective amount of Abrakha Bhasma (Calyx of Mica), Jaiphal (Myristica fragrans Houtt), Sunthi (Zingiber officinal Roscoe), Jivanti Ghana (Leptadenia reticulate), Haritaki Ghana (Terminalia chebula), Guduchi Ghana (Tinospora cordifolia), Shatavari Ghana (Asparagus racemosus), Dadima (Punica granatum Linn), Pippali (Piper longum Linn), and Loha Bhasma (Calyx of Iron).

2. The herbomineral composition according to claim 1 wherein the amount of Abrakha Bhasma is 25 mg, Jaiphal is 25 mg, Sunthi is 25 mg, Jivanti Ghana is 37.5 mg, Haritaki Ghana is 25 mg, Guduchi Ghana is 37.5 mg, Shatavari Ghana is 25 mg, Dadima is 12.5 mg, Pippali is 37.5 mg, and Loha Bhasma is 12.5 mg.

3. The herbomineral composition according to claim 1 in the form of liquid, powder, granules, tablets or capsules with excipients.

4. The herbomineral composition according to claim 1 further comprising an effective amount of Kajjali, made from equal portion of Mercury and Ghandhak (sulphur).

5. The herbomineral composition according to claim 4 wherein the amount of Kajjali is 50 mg.

6. The herbomineral composition according to claim 4 wherein the amount of Kajjali is 50 mg, Abrakha Bhasma is 12.5 mg, Jaiphal is 25 mg, Sunthi is 25 mg, Jivanti Ghana is 25 mg, Haritaki Ghana is 25 mg, Guduchi Ghana is 12.5 mg, Shatavari Ghana is 12.5 mg, Dadima is 12.5 mg, Pippali is 37.5 mg, and Loha Bhasma is 12.5 mg.

7. A method of treating sickle cell disease, the method comprising orally administering to a human in need of treatment for sickle cell disease a herbomineral composition comprising an effective amount of Abrakha Bhasma (Calyx of Mica), Jaiphal (Myristica fragrans Houtt), Sunthi (Zingiber officinal Roscoe), Jivanti Ghana (Leptadenia reticulate), Haritaki Ghana (Terminalia chebula), Guduchi Ghana (Tinospora cordifolia), Shatavari Ghana (Asparagus racemosus), Dadima (Punica granatum Linn), Pippali (Piper longum Linn), and Loha Bhasma (Calyx of Iron).

8. The method of treating sickle cell disease according to claim 7 wherein the amount of Abrakha Bhasma is 25 mg, Jaiphal is 25 mg, Sunthi is 25 mg, Jivanti Ghana is 37.5 mg, Haritaki Ghana is 25 mg, Guduchi Ghana is 37.5 mg, Shatavari Ghana is 25 mg, Dadima is 12.5 mg, Pippali is 37.5 mg, and Loha Bhasma is 12.5 mg.

9. The method of treating sickle cell disease according to claim 8 wherein the composition is orally administered in the form of liquid, suspension, powder, granules, tablets or capsules with excipients.

10. The method of treating sickle cell disease according to claim 9 wherein the composition is administered in one to three times per day for adults.

11. The method of treating sickle cell disease according to claim 9 wherein the composition is administered once a day to children.

12. A method of treating sickle cell disease, the method comprising orally administering to a human in need of treatment for sickle cell disease a herbomineral composition comprising an effective amount of Kajjali (made from equal proportion of Mercury and Ghandhak (sulphur)), Abrakha Bhasma (Calyx of Mica), Jaiphal (Myristica fragrans Houtt), Sunthi (Zingiber officinal Roscoe), Jivanti Ghana (Leptadenia reticulate), Haritaki Ghana (Terminalia chebula), Guduchi Ghana (Tinospora cordifolia), Shatavari Ghana (Asparagus racemosus), Dadima (Punica granatum Linn g), Pippali (Piper longum Linn), and Loha Bhasma (Calyx of Iron).

13. The method of treating sickle cell disease according to claim 12 wherein the amount of Kajjali is 50 mg, Abrakha Bhasma is 12.5 mg, Jaiphal is 25 mg, Sunthi is 25 mg, Jivanti Ghana is 25 mg, Haritaki Ghana is 25 mg, Guduchi Ghana is 12.5 mg, Shatavari Ghana is 12.5 mg, Dadima is 12.5 mg, Pippali is 37.5 mg, and Loha Bhasma is 12.5 mg.

14. The method of treating sickle cell disease according to claim 12 wherein the composition is administered in the form of liquid, suspension, powder, tablets or capsules once or twice a day.

* * * * *